US009157898B1

(12) United States Patent
Steiner

(10) Patent No.: US 9,157,898 B1
(45) Date of Patent: *Oct. 13, 2015

(54) ULTRASONIC RECEIVING CIRCUIT

(71) Applicant: Lutron Electronics Co., Inc., Coopersburg, PA (US)

(72) Inventor: James P. Steiner, Royersford, PA (US)

(73) Assignee: LUTRON ELECTRONICS CO., INC., Coopersburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/186,006

(22) Filed: Feb. 21, 2014

Related U.S. Application Data

(63) Continuation-in-part of application No. 13/947,732, filed on Jul. 22, 2013, which is a continuation of application No. 13/052,418, filed on Mar. 21, 2011, now Pat. No. 8,514,075.

(60) Provisional application No. 61/316,011, filed on Mar. 22, 2010.

(51) Int. Cl.
    *G08B 13/08* (2006.01)
    *G01N 29/34* (2006.01)

(52) U.S. Cl.
    CPC .................................. *G01N 29/348* (2013.01)

(58) Field of Classification Search
    CPC .................. H05B 37/0227; G08B 13/1627
    USPC ............. 340/545.3, 539.1, 539.26, 540, 541, 340/552, 554, 565, 567; 367/94, 98, 135, 367/138
    See application file for complete search history.

(56) References Cited

U.S. PATENT DOCUMENTS

| 4,254,483 | A | | 3/1981 | Vidovic |
| 4,360,905 | A | | 11/1982 | Hackett |
| 4,820,938 | A | * | 4/1989 | Mix et al. ...................... 307/117 |
| 4,973,837 | A | * | 11/1990 | Bradbeer ...................... 250/221 |
| 5,210,484 | A | | 5/1993 | Remillard et al. |
| 5,640,143 | A | * | 6/1997 | Myron et al. ................. 340/541 |
| 5,850,045 | A | | 12/1998 | Harada et al. |
| 6,697,757 | B2 | | 2/2004 | Eckel et al. |

(Continued)

OTHER PUBLICATIONS

Perkin Elmer Inc., Technical Note TN-1000: What is a Lock-In Amplifier?, 2000, 4 pages.

*Primary Examiner* — Tai T Nguyen
(74) *Attorney, Agent, or Firm* — Mark E. Rose; Philip N. Smith

(57) ABSTRACT

An ultrasonic occupancy sensor for detecting presence or absence of an occupant in a space includes an ultrasonic receiving circuit having a synchronous rectifier that allows the circuit to detect small-magnitude ultrasonic waves having a Doppler shift. The sensor comprises an ultrasonic transmitter for transmitting ultrasonic waves at an ultrasonic operating frequency, and a controller that drives the transmitting circuit with complementary drive signals to control the ultrasonic operating frequency. The synchronous rectifier receives the drive signals from the controller and rectifies an amplified input signal to generate a rectified signal, which is filtered by a filter to generate a filtered signal. The controller receives the filtered signal and determines that the space is occupied if the magnitude of the filtered signal exceeds a threshold. The ultrasonic occupancy sensor may also include a low phase-noise oscillator circuit coupled to the controller for setting an internal operating frequency of the controller.

28 Claims, 11 Drawing Sheets

(56) References Cited

U.S. PATENT DOCUMENTS

| | | |
|---|---|---|
| 6,914,552 B1 | 7/2005 | McEwan |
| 7,211,798 B2 | 5/2007 | Wu et al. |
| 7,884,727 B2 | 2/2011 | Tran |
| 8,514,075 B1 | 8/2013 | Steiner |
| 2010/0052574 A1 | 3/2010 | Blakeley et al. |
| 2010/0052576 A1 | 3/2010 | Steiner et al. |
| 2010/0052894 A1 | 3/2010 | Steiner et al. |
| 2010/0207759 A1 | 8/2010 | Sloan et al. |

* cited by examiner

ULTRASONIC RECEIVING CIRCUIT

CROSS-REFERENCE TO RELATED APPLICATIONS

This application is a continuation-in-part application of commonly-assigned U.S. patent application Ser. No. 13/947,732, filed Jul. 22, 2013, which is a continuation of U.S. patent application Ser. No. 13/052,418, filed Mar. 21, 2011, now U.S. Pat. No. 8,514,075, issued Aug. 20, 2013, which is a non-provisional application of commonly-assigned U.S. Provisional Application No. 61/316,011, filed Mar. 22, 2010, all entitled ULTRASONIC RECEIVING CIRCUIT, the entire disclosures of which are hereby incorporated by reference.

BACKGROUND OF THE INVENTION

1. Field of the Invention

The present invention relates to occupancy and vacancy sensors for detecting an occupancy or a vacancy in a space, and more particularly, to an ultrasonic receiving circuit for an occupancy or vacancy sensor.

2. Description of the Related Art

Occupancy and vacancy sensors are often used to detect occupancy and/or vacancy conditions in a space in order to control an electrical load, such as, for example, a lighting load. An occupancy sensor typically operates to turn on the lighting load when the occupancy sensor detects the presence of a user in the space (i.e., an occupancy event) and then to turn off the lighting load when the occupancy sensor detects that the user has left the space (i.e., a vacancy event). A vacancy sensor only operates to turn off the lighting load when the vacancy sensor detects a vacancy in the space. Therefore, when using a vacancy sensor, the lighting load must be turned on manually (e.g., in response to a manual actuation of a control actuator).

Occupancy and vacancy sensors have often been provided in wall-mounted load control devices that are coupled between an alternating-current (AC) power source and an electrical load for control of the amount of power delivered to the electrical load. Some prior art occupancy and vacancy sensors have been provided as part of lighting control systems. These sensors are often coupled via a wired control link to a lighting controller (e.g., a central processor), which then controls the lighting loads accordingly. Alternatively, the sensors may be battery-powered and may be operable to transmit wireless signals, such as radio-frequency (RF) signals, to load control devices, such as dimmer switches. These occupancy and vacancy sensors are not required to be mounted in electrical wallboxes, but may be mounted to the ceiling or high on a wall. Therefore, the occupancy and vacancy sensors may be positioned optimally to detect the presence of the user in all areas of the space.

The prior art occupancy and vacancy sensors typically comprise internal detectors, such as, for example, a pyroelectric infrared (PIR) detector, and a lens for directing energy to the PIR detector for detecting the presence of the user in the space. Alternatively, some prior art occupancy and vacancy sensors have included ultrasonic transmitting and receiving circuits for detecting the presence of the user in the space. Ultrasonic sensors transmit ultrasonic waves at a predetermined frequency, and analyze received ultrasonic waves to determine if there is an occupant in the space. The received ultrasonic waves that are reflected off of moving objects will be characterized by a Doppler shift with respect to the transmitted ultrasonic waves, while the received ultrasonic waves that are produced by reflections off of the walls, ceiling, floor, and other stationary objects of the room will not have a Doppler shift. Therefore, ultrasonic occupancy and vacancy sensors are able to determine if there is an occupant in the space if there is a Doppler shift between the frequencies of the transmitted and received ultrasonic waves.

Generally, the size of the objects that produce the ultrasonic waves having the Doppler shift (such as, a moving hand) are very small, and thus produce reflected ultrasonic waves having small magnitudes. One of the issues with detecting ultrasonic waves having a Doppler shift is that these received ultrasonic waves can be difficult to distinguish from the received ultrasonic waves that do not have a Doppler shift. A figure of merit for occupancy detection limits can be described using the signal-to-interference ratio (SIR), which is the ratio of the Doppler-shifted ultrasonic waves expressed in sound pressure level (SPL) to the non-Doppler-shifted ultrasonic waves.

The standard implementations for detecting Doppler shifts in ultrasonic waves take three standard forms. The first form uses a phase-lock-loop (PLL) integrated circuit (IC), such as, for example, part number CD74HC7046, manufactured by Texas Instruments Incorporated. In this implementation, the received ultrasonic waves are amplified by a pre-amplifier and then compared with a single fixed threshold (e.g., 100 mV) using a comparator to yield a binary waveform. The binary waveform is then applied to an exclusive-or (XOR) gate where the second input to the XOR is a clock input (e.g., a 40-kHz clock signal) that also drives the ultrasonic transmitting circuit. The resulting signal is then passed through a band-pass filter to extract the Doppler signal. The resulting Doppler signal is then compared to a fixed threshold using another comparator to detect an occupancy or vacancy condition. The drawback of this implementation is that the circuit is very sensitive to the thresholds of the comparators and only works on signals with an SIR greater than approximately −40 dB.

The second prior art form for detecting Doppler shift implements the detection algorithm primarily within a microcontroller. In this implementation, the received ultrasonic waves are amplified by a preamplifier and then sampled using an analog-to-digital converter (e.g., an 8 to 12-bit ADC) in the microcontroller. The remainder of the algorithm is essentially the same as in the first prior art form for detecting Doppler shift described above except that the remainder of the algorithm of the second form is executed in the software of the microcontroller. This implementation depends on the accuracy of the ADC of the microcontroller and is limited by numerical noise due to the ADC quantization and the numerical precision used to calculate the results, which thus limits the ability to detect small-magnitude ultrasonic waves that have a Doppler shift.

The third prior art form is an amplitude-modulation (AM) demodulator, which, in its simplest form, uses a diode and a low-pass filter to form an envelope detector. The limitation of this circuit is that the received ultrasonic signal must have a minimum amplitude to render the diode conductive, thus reducing the ability of the circuit to detect small-magnitude ultrasonic waves that have a Doppler shift.

Thus, there is a need for a simple, effective low-cost ultrasonic receiving circuit for use in occupancy or vacancy sensors that avoids the disadvantages of the prior art.

SUMMARY OF THE INVENTION

As described herein, an ultrasonic receiving circuit for detecting the presence or absence of an occupant in a space comprises: (1) an ultrasonic receiving element for generating an ultrasonic input signal; (2) a synchronous rectifier for generating a rectified signal from the input signal, the synchronous rectifier comprising at least one amplifier circuit and at least one analog switch coupled to an output of the amplifier circuit for forming the rectified signal; and (3) a filter circuit for filtering the rectified signal to generate a filtered signal. The analog switch is rendered conductive and non-conductive to form the rectified signal such that the filtered signal indicates the presence of the occupant in the space.

An ultrasonic occupancy sensor for detecting presence or absence of an occupant in a space is also described herein. The occupancy sensor comprises an ultrasonic transmitting circuit having an ultrasonic transmitting element for transmitting ultrasonic waves, and an ultrasonic receiving circuit having an ultrasonic receiving element for receiving ultrasonic waves and generating an ultrasonic input signal. The ultrasonic receiving circuit further comprises an ultrasonic receiving element for receiving ultrasonic waves and generating an ultrasonic input signal, a synchronous rectifier for generating a rectified signal from the input signal, and a filter for filtering the rectified signal to generate a filtered signal. The synchronous rectifier comprises at least one amplifier circuit and at least one analog switch coupled to an output of the amplifier circuit for forming the rectified signal. The occupancy sensor further comprises a controller operable to drive the ultrasonic transmitting circuit with a drive signal to control an ultrasonic transmission frequency of the transmitted ultrasonic waves. The controller is operable to render the analog switch conductive and non-conductive in phase with the drive signal to form the rectified signal, receive the filtered signal, and determine that the space is occupied in response to the filtered signal.

Other features and advantages of the present invention will become apparent from the following description of the invention that refers to the accompanying drawings.

BRIEF DESCRIPTION OF THE DRAWINGS

The invention will now be described in greater detail in the following detailed description with reference to the drawings in which.

DETAILED DESCRIPTION OF THE INVENTION

Figure 1:
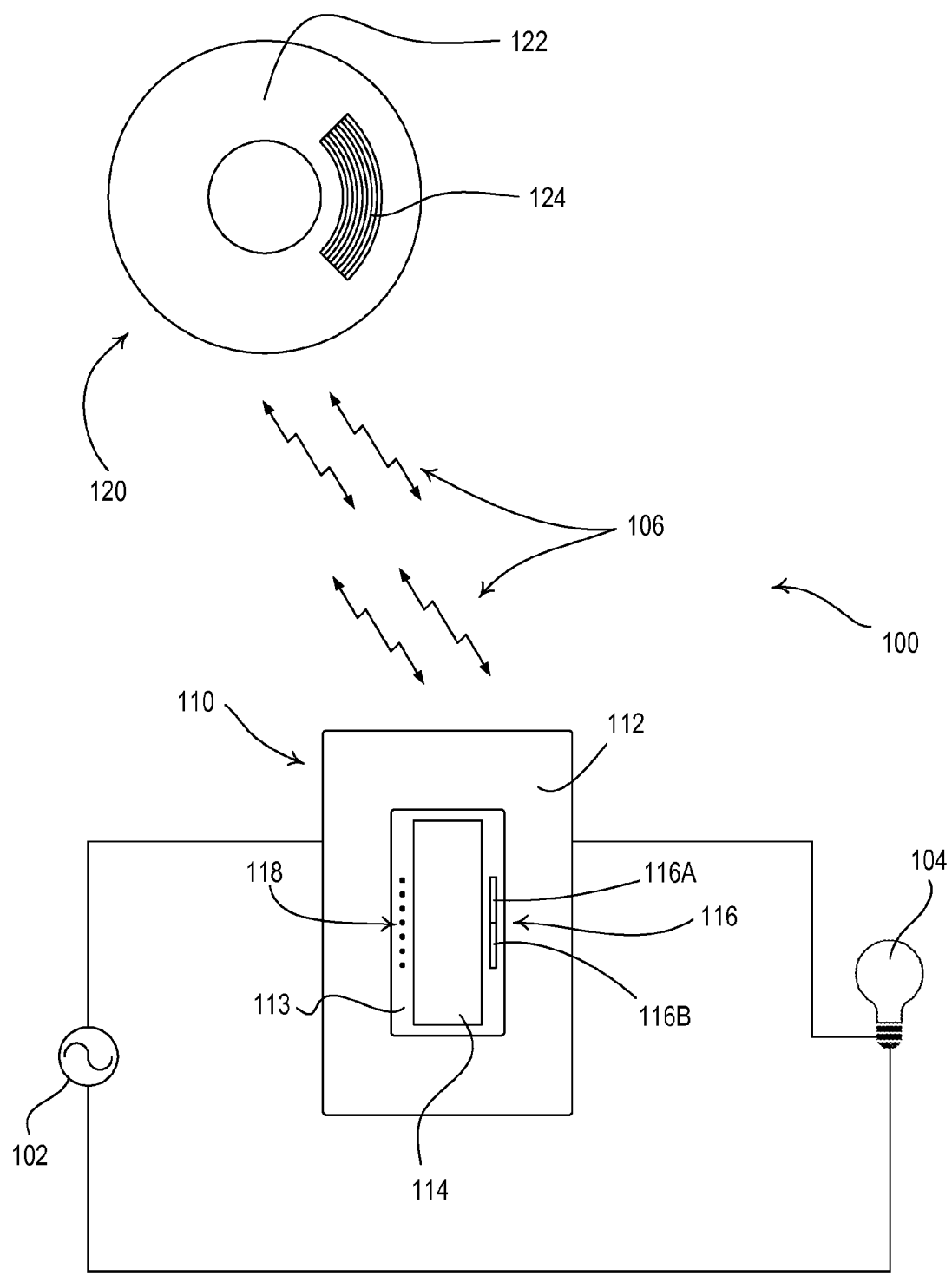
FIG. 1 is a simple diagram of a radio-frequency (RF) lighting control system having a dimmer switch and an ultrasonic occupancy sensor for controlling the amount of power delivered to a lighting load.

The foregoing summary, as well as the following detailed description of the preferred embodiments, is better understood when read in conjunction with the appended drawings. For the purposes of illustrating the invention, there is shown in the drawings an embodiment that is presently preferred, in which like numerals represent similar parts throughout the several views of the drawings, it being understood, however, that the invention is not limited to the specific methods and instrumentalities disclosed.

FIG. 1 is a simple diagram of a radio-frequency (RF) lighting control system 100 comprising a dimmer switch 110 and a remote ultrasonic occupancy sensor 120. The dimmer switch 110 is adapted to be coupled in series electrical connection between an AC power source 102 and a lighting load 104 for controlling the amount of power delivered to the lighting load. The dimmer switch 110 may be adapted to be wall-mounted in a standard electrical wallbox. Alternatively, the dimmer switch 110 could be implemented as a table-top load control device. The dimmer switch 110 comprises a faceplate 112 and a bezel 113 received in an opening of the faceplate. The dimmer switch 110 further comprises a toggle actuator 114, i.e., a button, and an intensity adjustment actuator 116. Successive actuations of the toggle actuator 114 toggle, i.e., turn off and on, the lighting load 104. Actuations of an upper portion 116A or a lower portion 116B of the intensity adjustment actuator 116 respectively increase or decrease the amount of power delivered to the lighting load 104 and thus increase or decrease the intensity of the lighting load 104 from a minimum intensity (e.g., 1%) to a maximum intensity (e.g., 100%). A plurality of visual indicators 118, e.g., light-emitting diodes (LEDs), are arranged in a linear array on the left side of the bezel 113. The visual indicators 118 are illuminated to provide feedback of the intensity of the lighting load 104. An example of a dimmer switch having a toggle actuator 114 and an intensity adjustment actuator 116 is described in greater detail in U.S. Pat. No. 5,248,919, issued Sep. 29, 1993, entitled LIGHTING CONTROL DEVICE, the entire disclosure of which is hereby incorporated by reference. Examples of a dimmer switch operable to transmit and receive digital messages is described in greater detail in U.S. patent application Ser. No. 12/033,223, filed Feb. 19, 2008, entitled COMMUNICATION PROTOCOL FOR A RADIO-FREQUENCY LOAD CONTROL SYSTEM, the entire disclosure of which is hereby incorporated by reference.

The occupancy sensor 120 may be removably mountable to a ceiling or a wall, for example, in the vicinity of (i.e., a space around) the lighting load 104 controlled by the dimmer switch 110, such that the occupancy sensor is operable to detect an occupancy condition (i.e., the presence of the occupant) or a vacancy condition (i.e., the absence of the occupant) in the vicinity of the lighting load. The lighting control system 100 may comprise additional occupancy sensors 120 that are spaced apart so as to detect occupancy conditions in different areas of the vicinity of the lighting load 104. The occupancy sensor 120 is operable to transmit digital messages wirelessly via RF signals 106 to the dimmer switch 110 in response to detecting occupancy conditions or vacancy conditions in the space around the lighting load 104. The occupancy sensor 120 may be battery-powered, or may be connected to an external power source.

Figure 2:
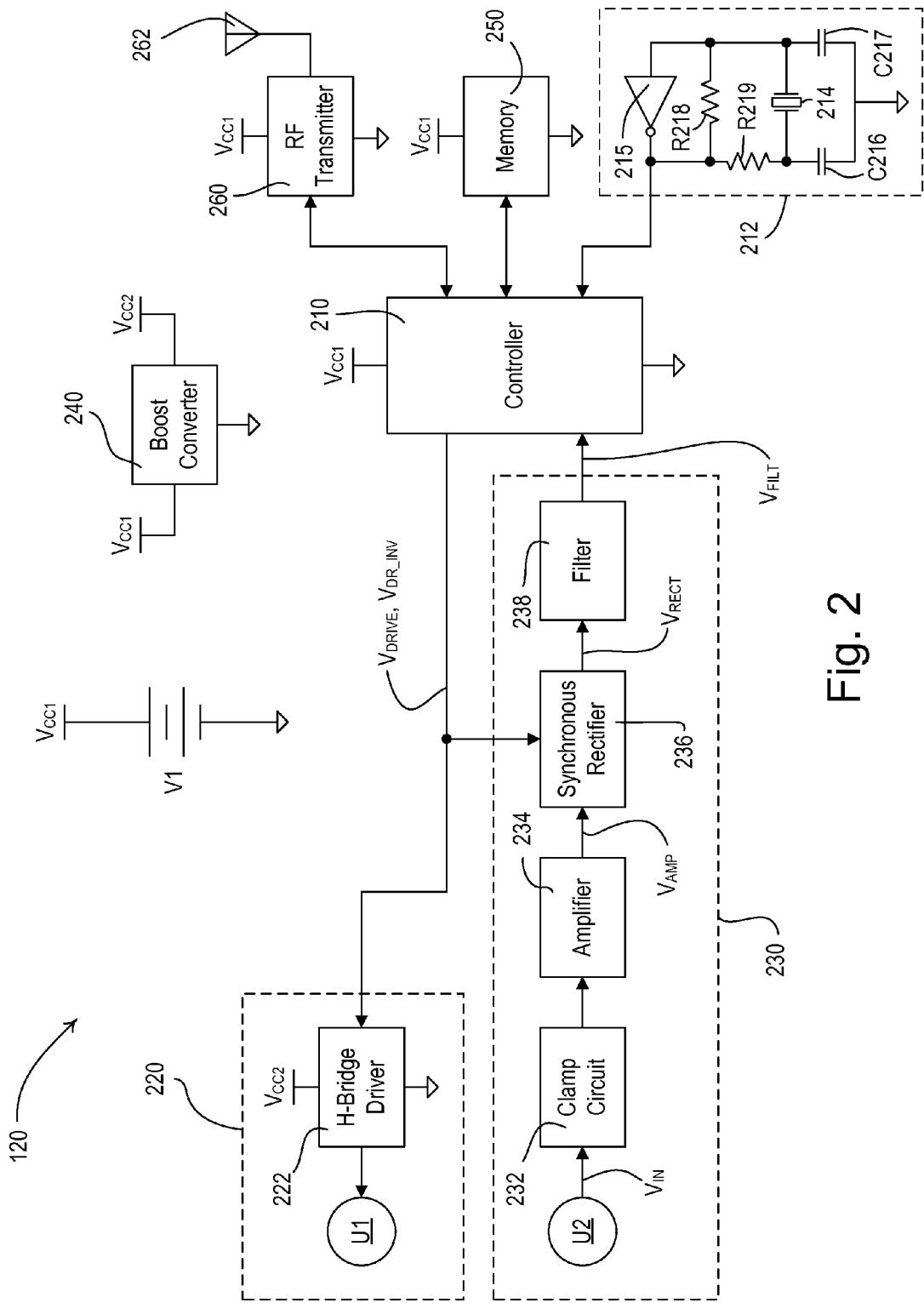
FIG. 2 is a simplified block diagram of an ultrasonic occupancy sensor that allows for detecting the presence or absence of an occupant in a space.

The occupancy sensor 120 has an occupancy sensing circuit comprising an internal ultrasonic transceiver, which is housed in an enclosure 122 and includes an ultrasonic transmitting element U1 (FIG. 2) and an ultrasonic receiving element U2 (FIG. 2). The enclosure 122 has a vent 124 for allowing ultrasonic waves to be transmitted by the ultrasonic transmitting element U1 and received by the ultrasonic receiving element U2. The occupancy sensor 120 is operable to determine whether occupancy conditions or vacancy conditions are presently occurring in the space in response to the ultrasonic waves received by the ultrasonic receiving element U2 as will be described in greater detail below. Alternatively, the occupancy sensor 120 could additionally comprise a passive infrared (PIR) detector, a microwave detector, or any suitable detector or combination of detectors.

During a setup procedure of the RF lighting control system 100, the dimmer switch 110 may be assigned to (i.e., associated with) the occupancy sensor 120 (and to additional occupancy sensors). The setup and configuration of a lighting control system including occupancy sensors is described in greater detail in U.S. Pat. No. 8,199,010, issued Jun. 12, 2012, entitled METHOD AND APPARATUS FOR CONFIGURING A WIRELESS SENSOR, the entire disclosure of which is hereby incorporated by reference.

A message transmitted by the occupancy sensor 120 may include a command and identifying information, for example, a 52-bit serial number (i.e., a unique identifier) associated with the transmitting occupancy sensor. The dimmer switch 110 is responsive to messages containing the serial numbers of the occupancy sensors 120 to which the dimmer switch is assigned. The commands included in the digital messages transmitted by the occupancy sensor 120 may comprise an occupied command or a vacant command. When the lighting load 104 is off, the dimmer switch 110 is operable to turn on the lighting load in response to receiving a first occupied command from any one of the occupancy sensors 120 to which the dimmer switch is assigned. The dimmer switch 110 is operable to turn off the lighting load 104 in response to the last vacant command received from those occupancy sensors 120 from which the occupancy sensor received occupied commands. For example, if two occupancy sensors 120 both transmit occupied commands to the dimmer switch 110, the dimmer switch will not turn off the lighting load 104 until subsequent vacant commands are received from both of the occupancy sensors. The operation of a lighting control system including wireless occupancy sensors is described is greater detail in U.S. Pat. No. 8,009,042, issued Aug. 30, 2012, entitled RADIO-FREQUENCY LIGHTING CONTROL SYSTEM WITH OCCUPANCY SENSING, the entire disclosure of which is hereby incorporated by reference.

Figure 3A:
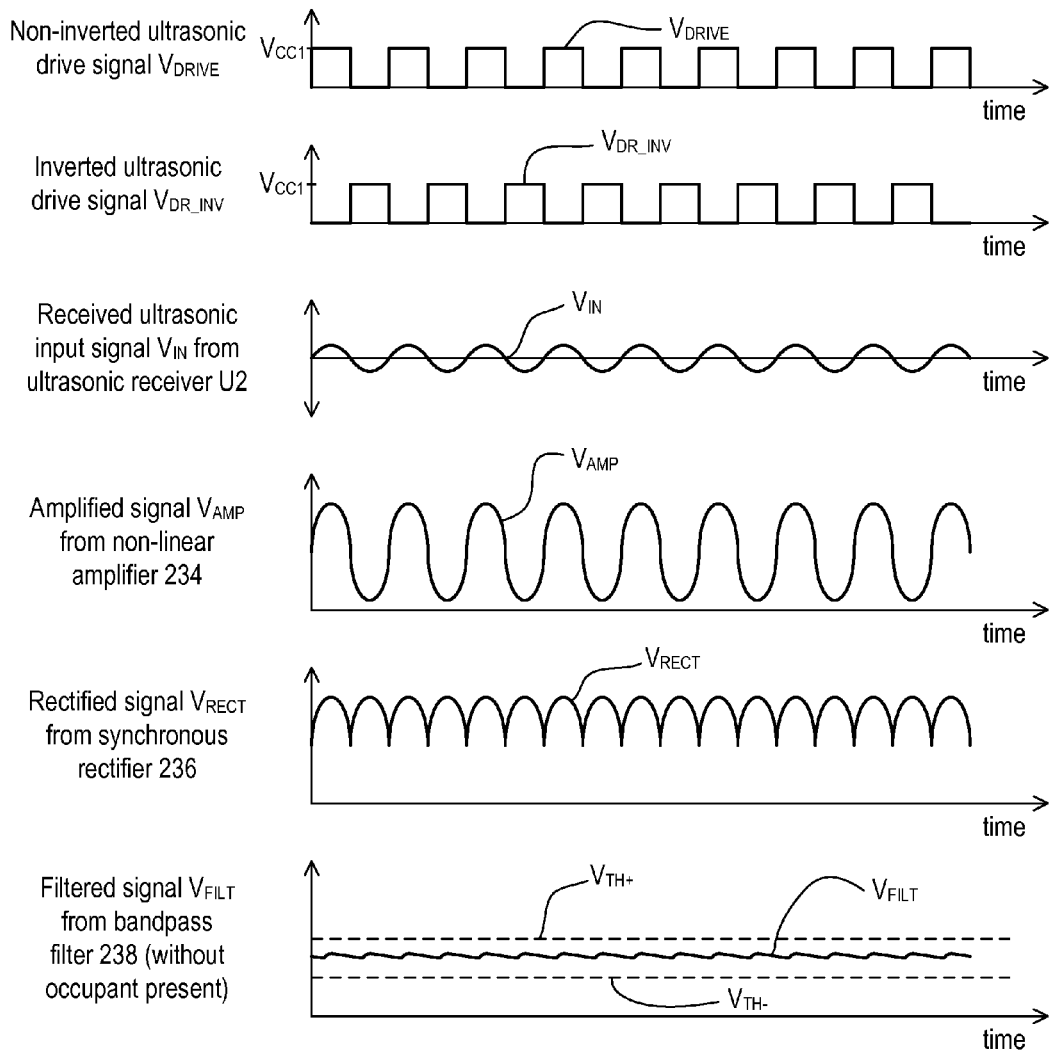
FIG. 3A shows example waveforms illustrating the operation of an ultrasonic receiving circuit of an occupancy sensor when there is not an occupant in a space.
Figure 3B:
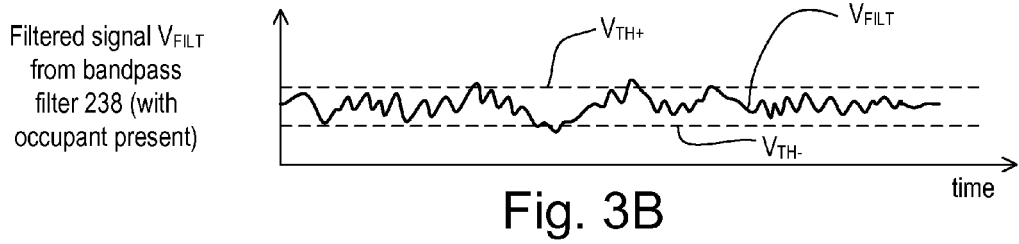
FIG. 3B shows an example waveform that illustrates the operation of an ultrasonic receiving circuit of an occupancy sensor when there is an occupant in a space.

FIG. 2 is a simplified block diagram of an occupancy sensor 200 (e.g., the occupancy sensor 120 of the lighting control system 100). FIG. 3A shows example waveforms illustrating the operation of the occupancy sensor 200 when there is not an occupant in the space, and FIG. 3B shows an example waveform illustrating the operation of the occupancy sensor 200 when there is an occupant in the space. The occupancy sensor 200 comprises a controller 210 coupled to an ultrasonic transmitting circuit 220 for transmitting the ultrasonic waves and an ultrasonic receiving circuit 230 for receiving the ultrasonic waves to thus detect the presence and absence of the occupant in the space. For example, the controller 210 may be a microprocessor, but may alternatively be any suitable processing device, such as a programmable logic device (PLD), a microcontroller, an application specific integrated circuit (ASIC), or a field-programmable gate array (FPGA). The ultrasonic transmitting circuit 220 comprises the ultrasonic transmitting element U1 and the ultrasonic receiving circuit 230 comprises the ultrasonic receiving element U2. The ultrasonic transmitting element U1 and the ultrasonic receiving element U2 may both comprise, for example, piezoelectric elements.

The controller 210 is coupled to a low phase-noise oscillator circuit 212 for setting an internal operating frequency $f_{OP}$ of the controller (e.g. approximately 40 kHz). The low phase-noise oscillator circuit 212 may comprise, for example, a Pierce oscillator circuit as shown in FIG. 2 having a crystal 214, such as a 40-kHz piezoelectric crystal, e.g., part number CM250C, manufactured by Citizen Crystal. For example, the low phase-noise oscillator circuit 212 may be characterized by a spectral purity of approximately −60 dBc at 5 Hz from the rated frequency (i.e., 40 kHz). The low phase-noise oscillator circuit 212 further comprises an inverter 215, two capacitors C216, C217 (e.g., each having a capacitance of approximately 12 pF), and two resistors R218, R219 (e.g., having resistances of approximately 10 MΩ and 392 kΩ, respectively). Alternatively, the low phase-noise oscillator circuit 212 could comprise any suitable external low phase-noise oscillator circuit, or an internal low phase-noise oscillator circuit of the controller 210.

The occupancy sensor 200 comprises a battery V1 that generates a direct-current (DC) supply voltage $V_{CC1}$ (e.g., approximately 3 volts) for powering the controller 210 and the ultrasonic receiving circuit 230. The occupancy sensor 200 further comprises a boost converter 240 that receives the supply voltage $V_{CC1}$ and generates a boosted voltage $V_{CC2}$ (e.g., approximately 12 volts) for powering the ultrasonic transmitting circuit 220. The controller 210 is further coupled to a memory 250 for storage of operating characteristics of the occupancy sensor 200. The memory 250 may be implemented as an external integrated circuit (IC) or as an internal circuit of the controller 210. The occupancy sensor 200 further comprises an RF transmitter 260 coupled to the controller 210 and an antenna 262 for transmitting the RF signals 106. Alternatively, the occupancy sensor 200 could comprise an RF transceiver to allow for two-way communication, for example, between the occupancy sensor 120 and the dimmer switch 110 in the lighting control system 100.

The ultrasonic transmitting circuit 220 may comprise a standard H-bridge drive circuit 222 for energizing the piezoelectric element (i.e., the ultrasonic transmitter U1). Specifically, the controller 210 drives the H-bridge drive circuit 222 with a non-inverted ultrasonic drive signal $V_{DRIVE}$ and an inverted ultrasonic drive signal $V_{DR\_INV}$, which may both comprise complementary square wave signals as shown in FIG. 3A. The controller 210 generates the non-inverted ultrasonic drive signal $V_{DRIVE}$ and the inverted ultrasonic drive signal $V_{DR\_INV}$ such that both signals are characterized by an ultrasonic transmission frequency $f_{US}$, which may be equal to the operating frequency $f_{OP}$ of the controller (i.e., approximately 40 kHz). Since the operating frequency $f_{OP}$ of the controller 210 is derived from the low phase-noise oscillator circuit 212, the non-inverted ultrasonic drive signal $V_{DRIVE}$ and an inverted ultrasonic drive signal $V_{DR\_INV}$, and thus the ultrasonic transmission frequency $f_{US}$, are also characterized by low phase noise.

The ultrasonic receiver U2 of the ultrasonic receiving circuit 230 generates a received ultrasonic input signal $V_{IN}$ in response to the received ultrasonic waves. The input signal $V_{IN}$ is clamped by a clamp circuit 232 to protect the other circuitry of the ultrasonic receiving circuit 230. An amplifier circuit 234 (e.g., a non-linear amplifier) receives the input signal $V_{IN}$ and generates an amplified signal $V_{AMP}$. A gain $G_{NL}$ of the amplifier circuit 234 is approximately 11 when the magnitude of the AC component of the input signal $V_{IN}$ is small (e.g., less than approximately 1.2 volts), and approximately two (2) when the magnitude of the AC component of the input signal $V_{IN}$ is large (e.g., greater than approximately 1.2 volts). The ultrasonic receiving circuit 230 further comprises a synchronous rectifier 236 (i.e., a lock-in amplifier), which generates a rectified signal $V_{RECT}$ from the input signal $V_{IN}$. The synchronous rectifier 236 may receive the amplified signal $V_{AMP}$ (which is representative of the input signal $V_{IN}$) from the amplifier circuit 234 for generating the rectified signal $V_{RECT}$. The synchronous rectifier 236 may also receive at least one drive signal and may receive both the non-inverted ultrasonic drive signal $V_{DRIVE}$ and the inverted ultrasonic drive signal $V_{DR\_INV}$ from the controller 210.

A filter circuit 238 (e.g., an anti-aliasing filter, such as a bandpass filter) generates a filtered signal $V_{FILT}$ from the rectified signal $V_{RECT}$ and has a bandwidth of approximately 5-100 Hz. The controller 210 receives the filtered signal $V_{FILT}$ from the filter 238 circuit and includes, for example, an analog-to-digital converter (ADC) for sampling the filtered signal. The controller 210 is operable to detect the presence of the occupant in the space if the magnitude of the filtered signal rises above an upper voltage threshold $V_{TH+}$ (e.g., approximately 0.25 volts) or falls below a lower voltage threshold $V_{TH-}$ (as shown in FIG. 3B). Since the filtered signal $V_{FILT}$ is biased to approximately one-half of the supply voltage $V_{CC1}$ (i.e., approximately 1.5 volts), the filtered signal $V_{FILT}$ will have a DC magnitude equal to approximately 1.5 volts and will remain between the upper voltage threshold $V_{TH+}$ and the lower voltage threshold $V_{TH-}$ if there is not an occupant in the space (as shown in FIG. 3A). The upper voltage threshold $V_{TH+}$ and the lower voltage threshold $V_{TH-}$ may be predetermined fixed values or may be adjustable by the controller 210. In addition, the controller 210 may be operable to digitally filter the filtered signal $V_{FILT}$ received from the filter circuit 238 to provide additional filtering of the signal before determining if the space is occupied or unoccupied.

The synchronous rectifier 236 eliminates many of the limitations of the prior art. The synchronous rectifier 236 can work on input signals having very small magnitudes and is not limited by an ADC and numerical precisions of a microcontroller. Design principles and testing have demonstrated that signals with an SIR of −80 dB can easily be detected using the synchronous rectifier 236 of the ultrasonic receiving circuit 230 of the embodiments of the present invention.

Figure 4:
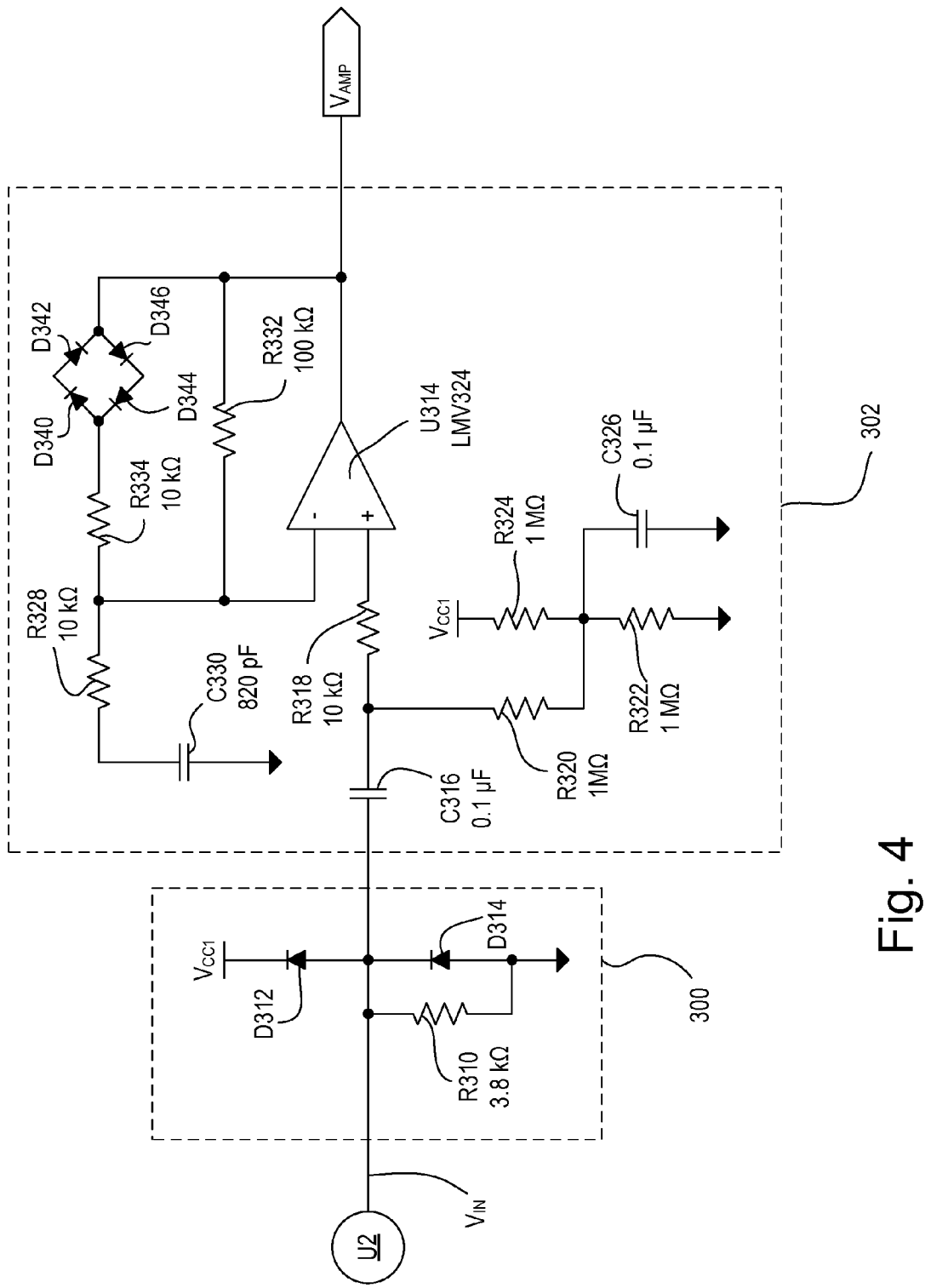
FIG. 4 is a simplified circuit diagram of examples of a clamp circuit and a non-linear amplifier of an ultrasonic receiving circuit of an occupancy sensor.
Figure 5:
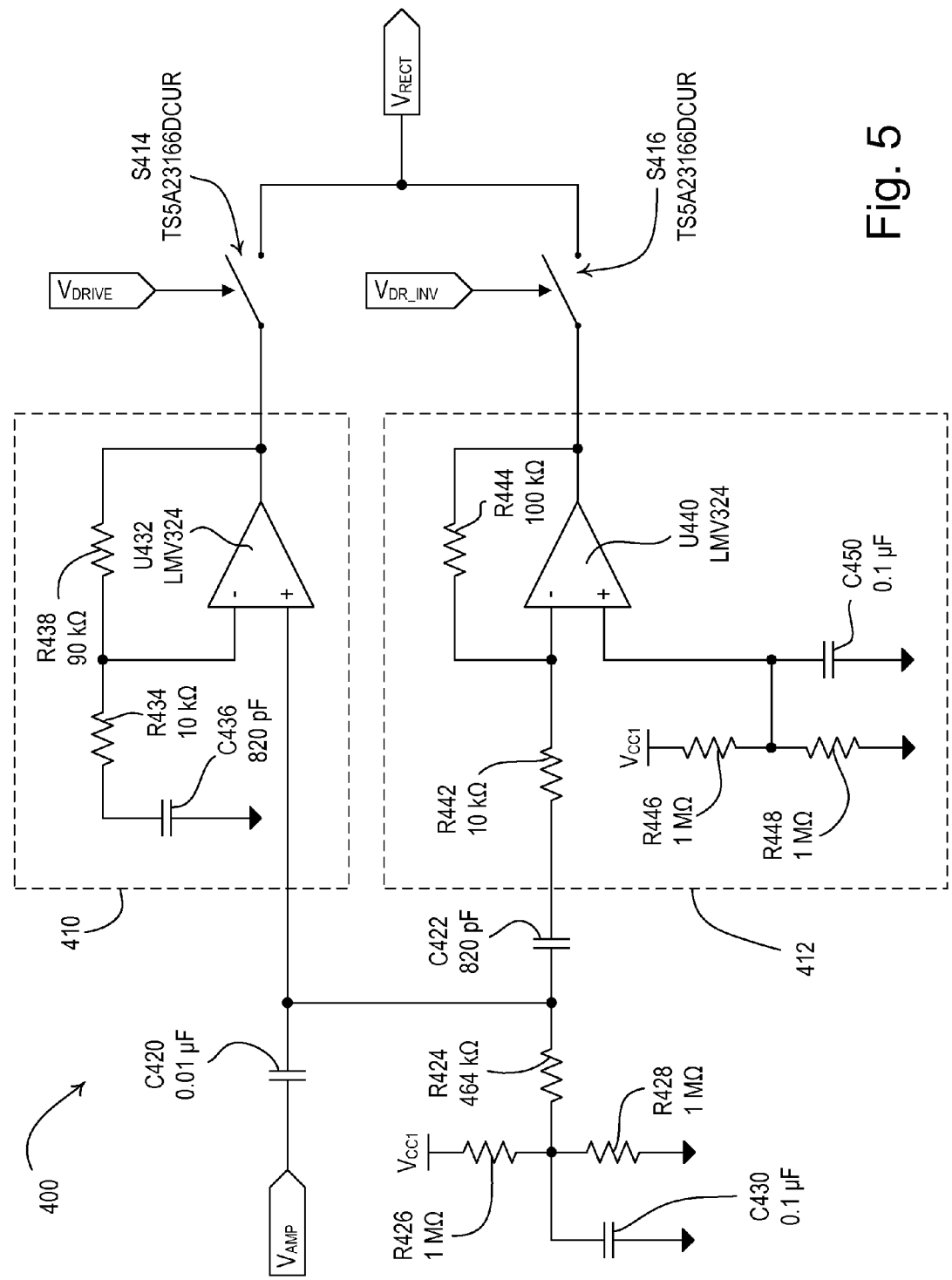
FIG. 5 is a simplified circuit diagram of an example of a synchronous rectifier of an ultrasonic receiving circuit of an occupancy sensor.
Figure 6:
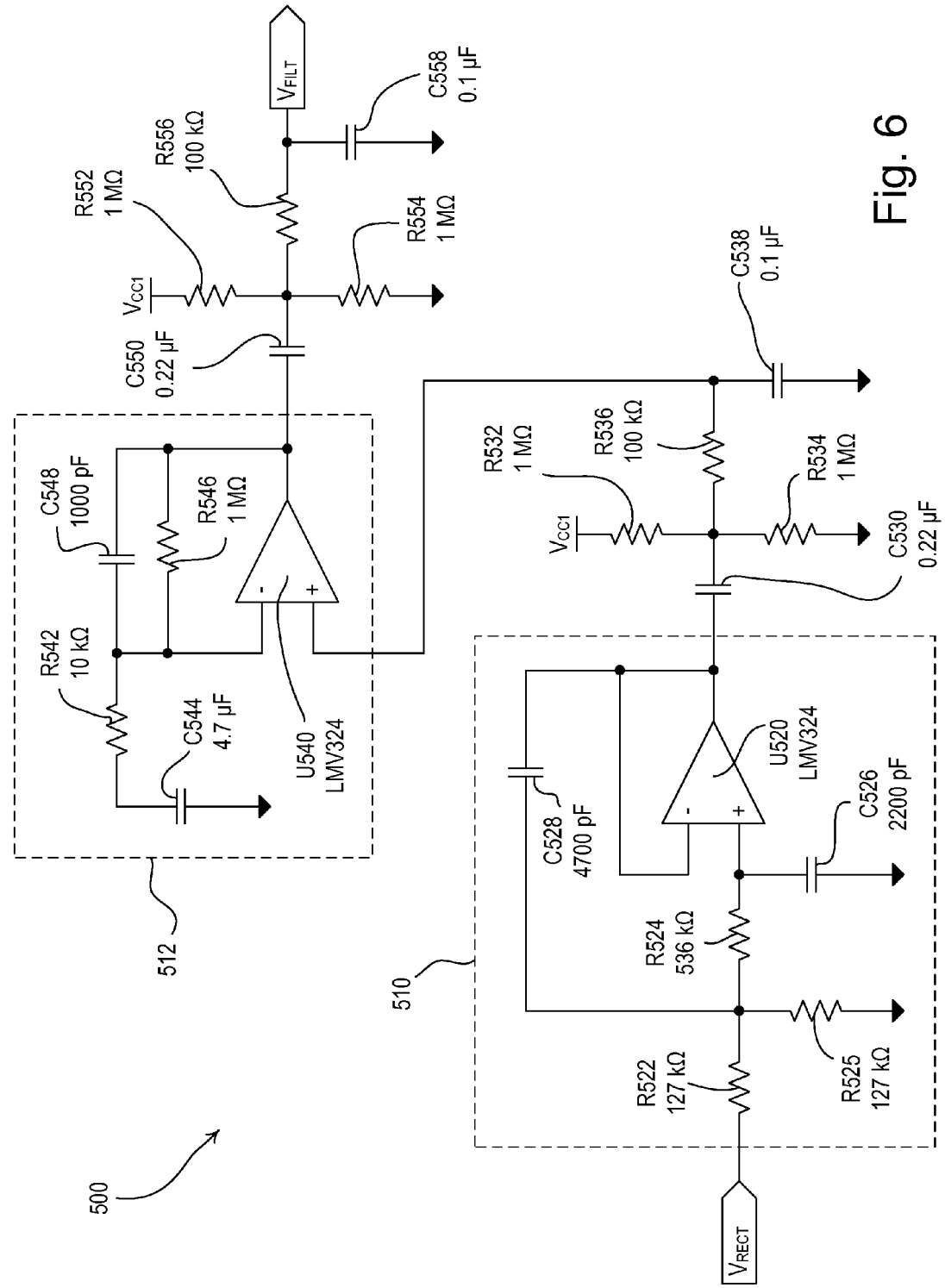
FIG. 6 is a simplified circuit diagram of an example of a bandpass filter of an ultrasonic receiving circuit of an occupancy sensor.

FIGS. 4-6 are simplified circuit diagrams of an ultrasonic receiving circuit (e.g., the ultrasonic receiving circuit 230 of the occupancy sensor 200 shown in FIG. 2). FIG. 4 is a simplified circuit diagram showing examples of a clamp circuit 300 (e.g., the clamp circuit 232) and a non-linear amplifier 302 (e.g., the amplifier circuit 234) of the ultrasonic receiving circuit. The clamp circuit 300 comprises a resistor R310 coupled between the coupled between the output of the ultrasonic receiver U2 and circuit common, a first diode D312 coupled between the output of the ultrasonic receiver U2 and the supply voltage $V_{CC1}$, and a second diode D314 coupled between circuit common and the output of the ultrasonic receiver U2. Accordingly, the magnitude of the input voltage $V_{IN}$ is prevented from rising above a diode drop (e.g. approximately 0.7 volts) above the magnitude of the supply voltage $V_{CC1}$, and from dropping below a diode drop below the circuit common.

The non-linear amplifier circuit 302 comprises an operational amplifier (op amp) U314. The input voltage $V_{IN}$ is coupled to the non-inverting input of the op amp U314 via a capacitor C316 and a resistor R318. A circuit (comprising resistors R320, R322, R324 and a capacitor C326) is coupled to the junction of the capacitor C316 and the resistor R318, and operates to reference the input voltage $V_{IN}$ at one-half of the supply voltage $V_{CC1}$. The inverting input of the op amp U314 is coupled to circuit common through a resistor R328 and a capacitor C330, and to the output via a resistor R332. The non-linear amplifier circuit 302 also comprises a resistor R344 and a plurality of diodes D340, D342, D344, D346 coupled between the inverting input and the output of the op amp U314.

When the magnitude of the AC component of the input signal $V_{IN}$ is small (i.e., less than approximately 1.2 volts), the diodes D340, D342, D344, D346 are non-conductive and only the resistor R332 is coupled between the inverting input and the output of the op amp U314, such that the gain $G_{NL}$ of the non-linear amplifier 302 is approximately 11. When the magnitude of the AC component of the input signal $V_{IN}$ is large (i.e., greater than approximately 1.2 volts), the either the diodes D340, D342 or the diodes D344, D346 become conductive and the resistor R334 is coupled in parallel with the resistor R332. As a result, the equivalent resistance coupled between the inverting input and the output of the op amp U314 decreases and the gain $G_{NL}$ of the non-linear amplifier 302 decreases to approximately 2. Specifically, when the magnitude of the voltage at the output of the op amp U314 is less than the magnitude of the voltage at the inverting input by approximately the sum of the forward voltages of the diodes D340, D342 (i.e., two diode drops, e.g., approximately 1.2 volts), the diodes D340, D342 are conductive. When the magnitude of the voltage at the output of the op amp U314 is greater than the magnitude of the voltage at the inverting input by approximately two diode drops, the diodes D344, D346 are conductive. Accordingly, the non-linear amplifier 302 amplifies the input signal $V_{IN}$ by a greater amount when the magnitude of the input signal $V_{IN}$ is small than when the magnitude of the input signal $V_{IN}$ is large to thus generate the amplified signal $V_{AMP}$.

FIG. 5 is a simplified circuit diagram showing an example of a synchronous rectifier 400 (e.g., the synchronous rectifier 236) of the ultrasonic receiving circuit. The synchronous rectifier 400 comprises a non-inverting amplifier 410 and an inverting amplifier 412 that both receive an amplified voltage $V_{AMP}$ (e.g., the amplified signal generated by the non-linear amplifier 334 shown in FIG. 4). Specifically, the amplified signal $V_{AMP}$ is coupled to the non-inverting amplifier 410 via a capacitor C420 and is further coupled to the inverting amplifier 412 via a capacitor C422. A circuit (comprising resistors R424, R426, R428 and a capacitor C430) is coupled to the junction of the capacitors C440, C442, and operates to reference the amplified signal $V_{AMP}$ at one-half of the supply voltage $V_{CC1}$.

The non-inverting amplifier 410 comprises an op amp U432 and has a gain $G_{NI}$ of approximately 10. The inverting input of the op amp U432 is coupled to circuit common through a resistor R434 and a capacitor C436, and is coupled to the output through a resistor R438. The inverting amplifier 412 comprises an op amp U440 and has a gain $G_I$ of approximately −10. The inverting input of the op amp U440 is coupled to the capacitor C422 via a resistor R442 and to the output via a resistor R444. The non-inverting input of the op amp U440 is coupled to a circuit that comprises resistors R446, R448 and a capacitor C450 and operates to bias non-inverting input at one-half of the supply voltage $V_{CC1}$.

The outputs of the non-inverting amplifier 410 and the inverting amplifier 412 are coupled to respective analog switches S414, S416, which are rendered conductive and non-conductive on a complementary basis in response to the non-inverted ultrasonic drive signal $V_{DRIVE}$ and the inverted ultrasonic drive signal $V_{DR\_INV}$, respectively. The outputs of the analog switches S414, S416 are mixed together to form the rectified signal $V_{RECT}$ (e.g., as shown in FIG. 3A). When the non-inverted ultrasonic drive signal $V_{DRIVE}$ is high (i.e., approximately equal to the supply voltage $V_{CC1}$) and the first switch S414 is conductive, the rectified signal $V_{RECT}$ is equal to the output of the non-inverting amplifier 410. When the inverted ultrasonic drive signal $V_{DR\_INV}$ is high and the second switch S416 is conductive, the rectified signal $V_{RECT}$ is equal to the output of the inverting amplifier 412.

FIG. 6 is a simplified circuit diagram of an example of a bandpass filter 500 (e.g., the filter circuit 238 of the ultrasonic receiving circuit 230). The bandpass filter 500 comprises a low-pass filter stage 510 and a non-inverting amplifier stage 512. The low-pass filter stage 510 includes an op amp U520 having a non-inverting input coupled to receive the rectified voltage $V_{RECT}$ through two resistors R522, R524. The junction of the two resistors R522, R524 is coupled to circuit common through a resistor R525. The non-inverting input is also coupled to circuit common via a capacitor C526. The output of the op amp U520 is coupled directly to the inverting input and is coupled to the junction of the resistors R522, R524 through a capacitor C528. The output of the low-pass filter stage 510 is coupled to the non-inverting amplifier stage 512 via a circuit that includes two capacitors C530, C538, and three resistors R532, R534, R536. The low-pass filter stage 510 operates to filter out the 80-kHz components of the rectified voltage $V_{RECT}$.

The non-inverting amplifier stage 512 comprises an op amp U540 and has a gain $G_{BP}$ of approximately 100. The non-inverting input of the op amp U540 is coupled to the output of the low-pass filter stage 510 via the capacitor C530 and the resistor R536. The inverting input of the op amp U540 is coupled to circuit common through a resistor R542 and a capacitor C544, and is coupled to the output via a resistor R546. A capacitor C548 is also coupled between the inverting input and the output of the op amp U540 and provides additional low-pass filtering. The filtered voltage $V_{FILT}$ is generated from the output of the op amp U540 via a circuit that comprises two capacitors C550, C558 and three resistors R552, R554, R556. The resistors R552, R554 reference the filtered voltage $V_{FILT}$ at one-half of the supply voltage $V_{CC1}$ (e.g., as shown in FIG. 3A). The capacitors C526, C544, C550 provide high-pass filtering for the bandpass filter 500. Accordingly, the bandpass filter 500 has a band width of 5-100 Hz.

The controller 210 receives the filtered voltage $V_{FILT}$ and determines the presence or absence of the occupant in the space in response to the magnitude of the filtered voltage. Since the ultrasonic transmission frequency $f_{US}$ of the transmitted waves is dependent upon the non-inverted ultrasonic drive signal $V_{DRIVE}$ and the inverted ultrasonic drive signal $V_{DR\_INV}$ and the analog switches S414, S416 of the synchronous rectifier 236 are controlled in response to the non-inverted ultrasonic drive signal $V_{DRIVE}$ and the inverted ultrasonic drive signal $V_{DR\_INV}$, the synchronous rectifier circuit will properly rectify the amplified signal $V_{AMP}$ and the filtered voltage $V_{FILT}$ stays between the upper voltage threshold $V_{TH+}$ and the lower voltage threshold $V_{TH-}$ when there is not an occupant in the space. However, if there is an occupant in the space, there will be a Doppler shift in the received ultrasonic waves as compared to the transmitted ultrasonic waves. In addition, the frequency of the received ultrasonic waves will be varying with respect to time (i.e., the difference between frequencies of the received ultrasonic waves and the ultrasonic transmission frequency $f_{US}$ of the transmitted waves will vary with respect to time). Accordingly, rectified signal $V_{RECT}$ generated by the synchronous rectifier circuit 236 will vary in magnitude and the filtered voltage $V_{FILT}$ will become greater than the upper voltage threshold $V_{TH+}$ and or less than the lower voltage threshold $V_{TH-}$, thus signally that the space is occupied.

Figure 7:
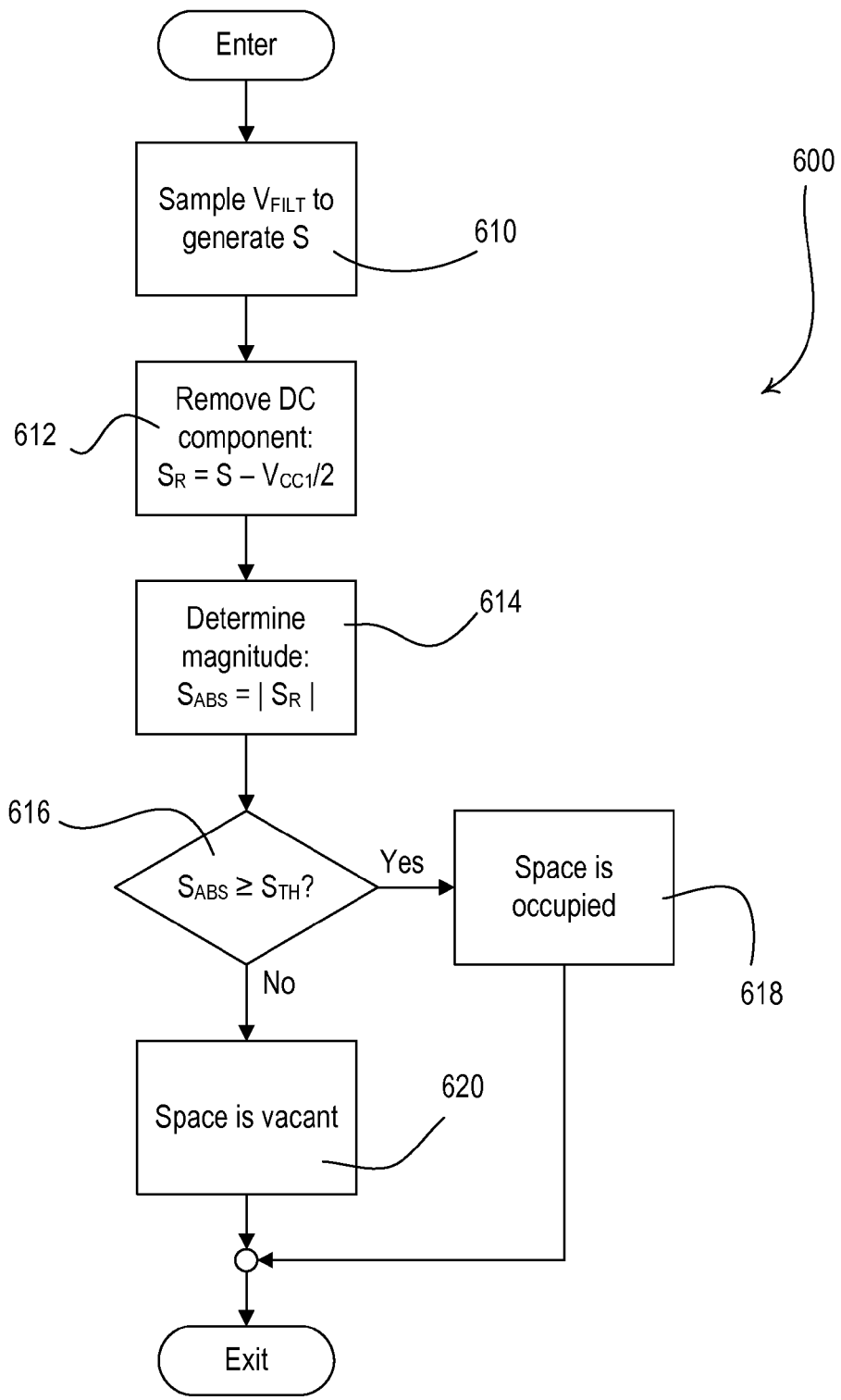
FIG. 7 is a simplified flowchart of a control procedure executed periodically by a controller of the occupancy sensor of FIG. 2.

FIG. 7 is a simplified flowchart of a control procedure 600 executed periodically by the controller 210 (e.g., approximately every two msec). The controller 210 first samples the filtered signal $V_{FILT}$ to generate a sample S at step 410. At step 612, the controller 210 removes the DC component of the sample S by subtracting one-half of the supply voltage $V_{CC1}$ from the sample (i.e., $S_R=S-V_{CC1}/2$). Next, the controller 210 determines the magnitude (i.e., the absolute value) of the sample S (i.e., $S_{ABS}=|S_R|$) at step 614. If the absolute value $S_{ABS}$ is greater than or equal to a sample threshold $S_{TH}$ at step 616, the controller 210 determines that the space is occupied at step 618 and the control procedure 600 exits. If the absolute value $S_{ABS}$ is less than the sample threshold $S_{TH}$ at step 616, the controller 210 determines that the space is vacant at step 620, before the control procedure 600 exits. For example, the sample threshold $S_{TH}$ may be equal to approximately one-half of the difference between the upper voltage threshold $V_{TH+}$ and the lower voltage threshold $V_{TH-}$ shown in FIGS. 3A and 3B, i.e., $S_{TH}=(V_{TH+}-V_{TH-})/2$.

In addition, the occupancy sensor 120 could additionally comprise a second occupancy sensing circuit including, for example, a passive infrared (PIR) detector, such that the occupancy sensor is a "dual-technology" occupancy sensor. Since the PIR detector uses different technology than the ultrasonic transmitting circuit 220 and the ultrasonic receiving circuit 230, the dual-technology occupancy sensor provides for an increased ability to detect the presence of an occupant in the space surrounding the occupancy sensor. An example of an occupancy sensing circuit having a PIR detector is described in greater detail in U.S. Pat. No. 7,940,167, issued May 10, 2011, entitled BATTERY-POWERED OCCUPANCY SENSOR, the entire disclosure of which is hereby incorporated by reference.

Figure 8:
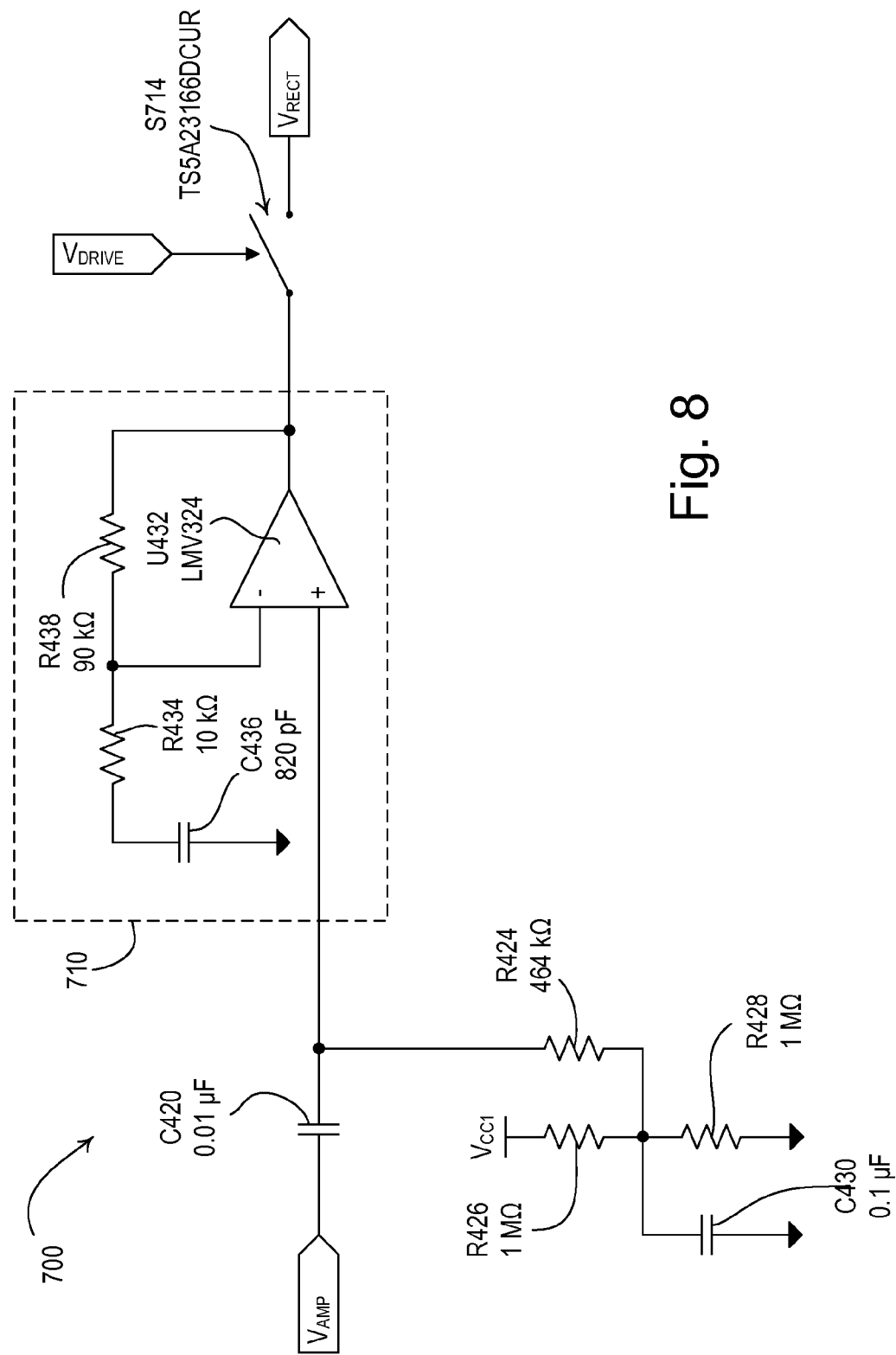
FIG. 8-11 are simplified circuit diagrams of alternate examples of synchronous rectifiers.

FIG. 8 is a simplified circuit diagram of an alternate example of a synchronous rectifier 700 (e.g., the synchronous rectifier 236 of the ultrasonic receiving circuit 230 shown in FIG. 2). The synchronous rectifier 700 is very similar to the synchronous rectifier 400 shown in FIG. 5. However, the synchronous rectifier 700 shown in FIG. 8 only comprises a non-inverting amplifier 710 (e.g., similar to the non-inverting amplifier 410) and does not also comprise an inverting amplifier (such as the inverting amplifier 412 shown in FIG. 5). The output of the non-inverting amplifier 710 is coupled to an analog switch S714, which is rendered conductive and non-conductive in response to a drive signal (e.g., the non-inverted ultrasonic drive signal $V_{DRIVE}$) to generate a half-wave rectified signal $V_{RECT}$. When the drive signal is high and the analog switch S714 is conductive, the magnitude of the rectified signal $V_{RECT}$ is equal to the output of the non-inverting amplifier 710. When the drive signal is low, the magnitude of the rectified signal $V_{RECT}$ is approximately zero volts.

Figure 9:
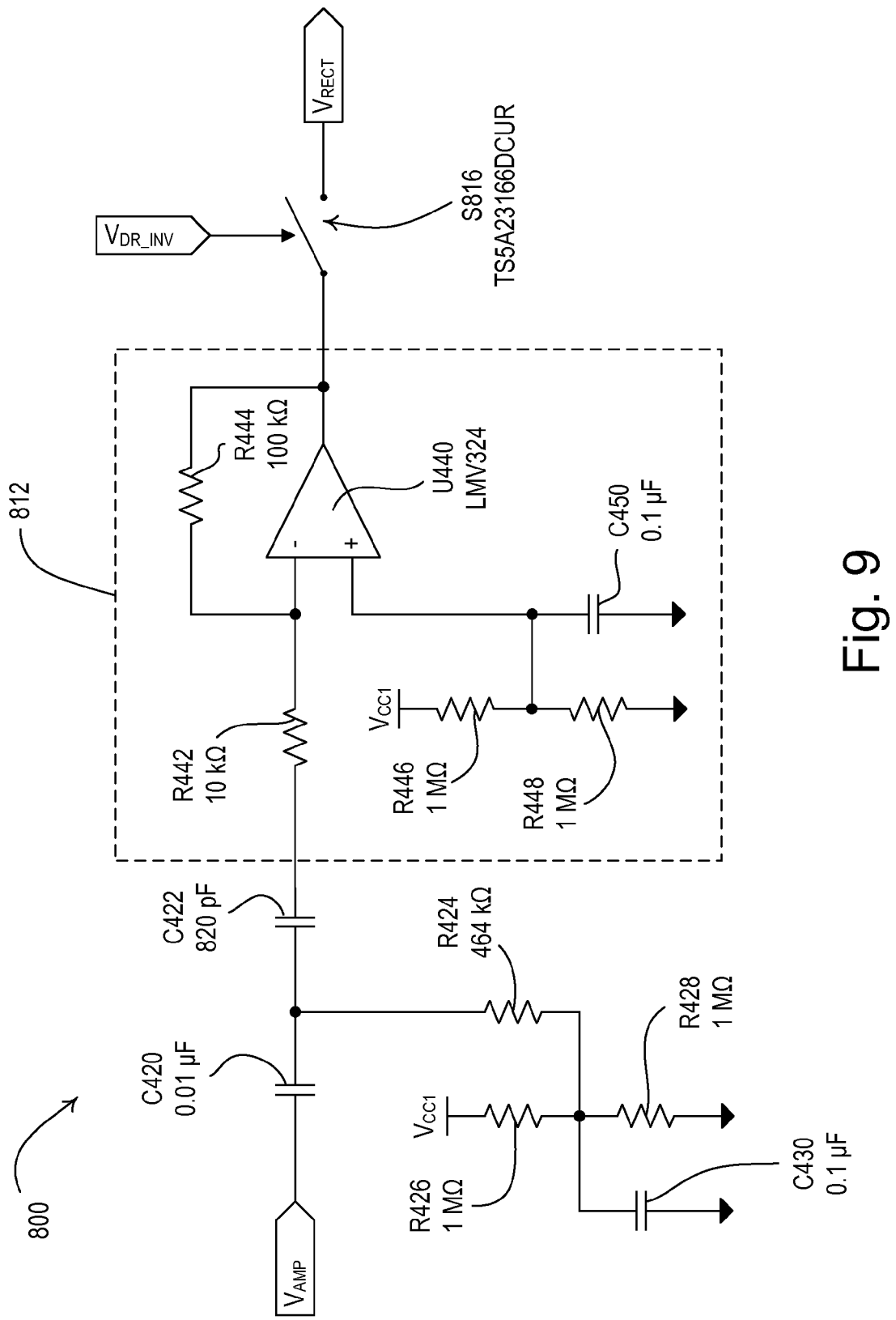

FIG. 9 is a simplified circuit diagram of another alternate example of a synchronous rectifier 800 (e.g., the synchronous rectifier 236 of the ultrasonic receiving circuit 230 shown in FIG. 2). The synchronous rectifier 800 is very similar to the synchronous rectifier 400 shown in FIG. 5. However, the synchronous rectifier 800 shown in FIG. 9 only comprises an inverting amplifier 812 (e.g., similar to the inverting amplifier 412) and does not also comprise a non-inverting amplifier (such as the non-inverting amplifier 410 shown in FIG. 5). The output of the inverting amplifier 812 is coupled to an analog switch S816, which is rendered conductive and non-conductive in response to a drive signal (e.g., the inverted ultrasonic drive signal $V_{DR\_INV}$) to generate a half-wave rectified signal $V_{RECT}$. When the drive signal is high and the analog switch S816 is conductive, the magnitude of the rectified signal $V_{RECT}$ is equal to the output of the inverting amplifier 812. When the drive signal is low, the magnitude of the rectified signal $V_{RECT}$ is approximately zero volts.

Figure 10:
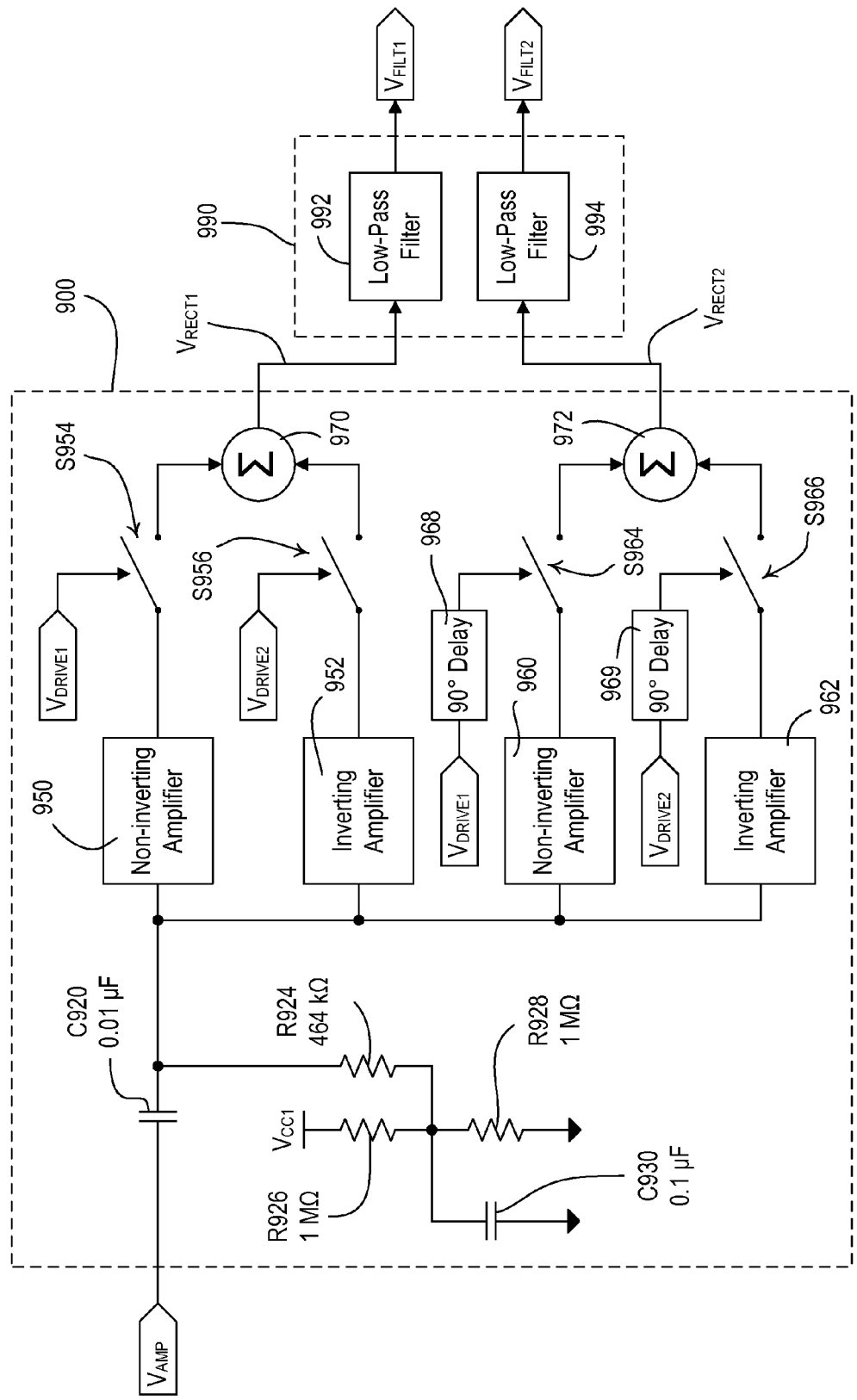

FIG. 10 is a simplified circuit diagram of another alternate example of a synchronous rectifier 900 and a filter circuit 990 (e.g., the synchronous rectifier 236 and the filter circuit 238, respectively, of the ultrasonic receiving circuit 230 shown in FIG. 2). The synchronous rectifier 900 comprises two pairs of non-inverting and inverting amplifiers, specifically, a first non-inverting amplifier 950 and a first inverting amplifier 952, and a second non-inverting amplifier 960 and a second inverting amplifier 962. The amplifiers 950, 952, 960, 962 all receive a signal (e.g., the amplified signal $V_{AMP}$ generated by the non-linear amplifier 334 shown in FIG. 4) via a capacitor C920. A circuit (comprising resistors R924, R926, R928 and a capacitor C930) is coupled to the inputs of the amplifiers 950, 952, 960, 962, and operates to reference the signal (e.g., the amplified signal $V_{AMP}$) at one-half of the supply voltage $V_{CC1}$. The first and second non-inverting amplifiers 950, 960 may each be similar to the non-inverting amplifier 410 shown in FIG. 5, while the first and second inverting amplifiers 952, 962 may each be similar to the inverting amplifier 412 shown in FIG. 5.

The outputs of the first non-inverting amplifier 950 and the first inverting amplifier 952 are coupled to respective analog switches S954, S956, which are rendered conductive and non-conductive on a complementary basis in response to first and second drive signals $V_{DRIVE1}$, $V_{DRIVE2}$, e.g., the non-inverted ultrasonic drive signal $V_{DRIVE}$ and the inverted ultrasonic drive signal $V_{DR\_INV}$, respectively. The outputs of the analog switches S954, S956 are summed together by a first summing circuit 970 to generate a first rectified voltage $V_{RECT1}$. The outputs of the second non-inverting amplifier 960 and the second inverting amplifier 962 are coupled to respective analog switches S964, S966, which are rendered conductive and non-conductive on a complementary basis in response to first and second phase-delayed drive signals, respectively (e.g., phase-delayed versions of the first and second drive signals, $V_{DRIVE1}$, $V_{DRIVE2}$). Specifically, the synchronous rectifier 900 comprises a first 90°-phase-delay circuit 968 that receives the first drive signal $V_{DRIVE1}$ and drives the analog switch S964, and a second 90°-phase-delay circuit 969 that receives the second drive signal $V_{DRIVE2}$ and drives the analog switch S966. The outputs of the analog switches S964, S966 are summed together by a second summing circuit 972 to generate a second rectified voltage $V_{RECT2}$, which provides the quadrature component of the amplified voltage $V_{AMP}$.

The filter circuit 990 comprises two low-pass filters 992, 994. The first low-pass filter circuit 992 receives the first rectified voltage $V_{RECT1}$ and generates a first filtered voltage $V_{FILT1}$. The second low-pass filter circuit 994 receives the second rectified voltage $V_{RECT1}$ and generates a second filtered voltage $V_{FILT1}$. A controller (e.g., the controller 210 of the occupancy sensor 200 shown in FIG. 2) receives both of the filtered voltages $V_{FILT1}$, $V_{FILT2}$, which are sampled using respective analog-to-digital converters of the controller. The controller is configured to analyze both of the filtered voltages $V_{FILT1}$, $V_{FILT2}$ to detect the presence and/or absence of an occupant.

Figure 11:
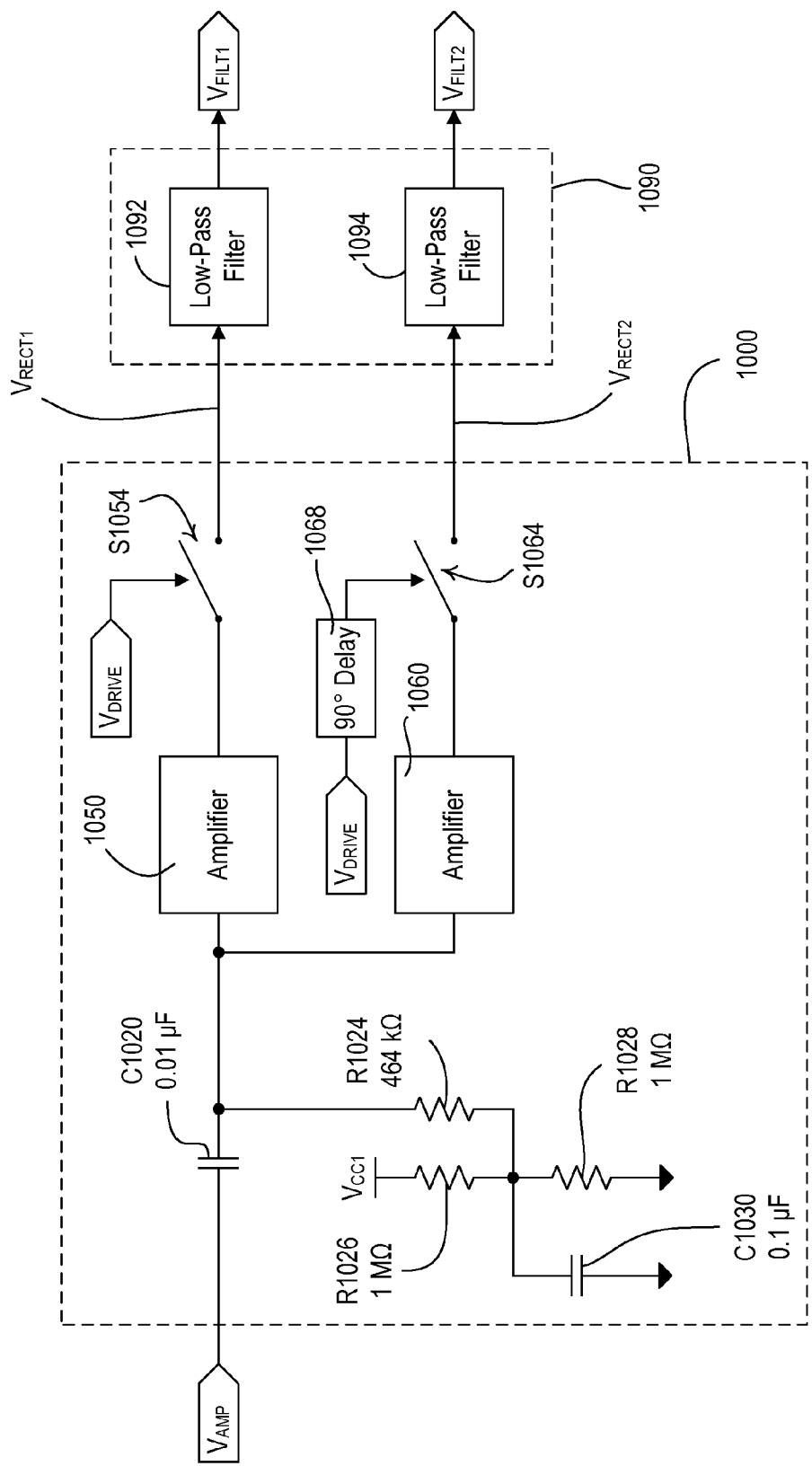

FIG. 11 is a simplified circuit diagram of another alternate example of a synchronous rectifier 1000 and a filter circuit 1090 (e.g., the synchronous rectifier 236 and the filter circuit 238, respectively, of the ultrasonic receiving circuit 230 shown in FIG. 2). The synchronous rectifier 1000 comprises two amplifiers 1050, 1060. For example, both amplifiers 1050, 1060 may comprise non-inverting amplifiers (which may each be similar to the non-inverting amplifier 410 shown in FIG. 5). Alternatively, both amplifiers 1050, 1060 may comprise inverting amplifiers (which may each be similar to the inverting amplifier 412 shown in FIG. 5). Both amplifiers 1050, 1060 receive a signal (e.g., the amplified signal $V_{AMP}$ generated by the non-linear amplifier 334 shown in FIG. 4) via a capacitor C1020. A circuit (comprising resistors R1024, R1026, R1028 and a capacitor C1030) is coupled to the inputs of the amplifiers 1050, 1060, and operates to reference the signal (e.g., the amplified signal $V_{AMP}$) at one-half of the supply voltage $V_{CC1}$.

The output of the first amplifier 1050 is coupled to a first analog switch S1054, which is rendered conductive and non-conductive in response to a drive signal $V_{DRIVE}$ (e.g., the non-inverted ultrasonic drive signal $V_{DRIVE}$ or the inverted ultrasonic drive signal $V_{DR\_INV}$) to generate a first rectified voltage $V_{RECT1}$. The synchronous rectifier 1000 comprises a 90°-phase-delay circuit 1068 that receives the drive signal $V_{DRIVE}$ and generates a phase-delayed drive signal. The output of the second amplifier 1060 is coupled to a second analog switch S1064 that is driven by the phase-delayed drive signal for generating a second rectified voltage $V_{RECT2}$ (which provides the quadrature component of the amplified voltage $V_{AMP}$). The filter circuit 1090 comprises a first low-pass filter circuit 1092 (which receives the first rectified voltage $V_{RECT1}$ and generates a first filtered voltage $V_{FILT1}$) and a second low-pass filter circuit 1094 (which receives the second rectified voltage $V_{RECT1}$ and generates a second filtered voltage $V_{FILT1}$). A controller (e.g., the controller 210 of the occupancy sensor 200 shown in FIG. 2) is configured to sample both of the filtered voltages $V_{FILT1}$, $V_{FILT2}$ (e.g., using analog-to-digital converters) and analyze the filtered voltages $V_{FILT1}$, $V_{FILT2}$ to detect the presence and/or of an occupant.

While the present invention has been described with reference to the dimmer switch 110 for controlling the intensity of the lighting load 104, the concepts of the present invention could be applied to load control systems comprising other types of load control devices, such as, for example, fan-speed controls for fan motors, temperature control devices for control of heating, ventilation, and air-conditioning (HVAC) systems, electronic dimming ballasts for fluorescent loads, and drivers for light-emitting diodes (LEDs). Further, the concepts of the present invention could be used to control other types of electrical loads, such as, for example, fan motors or motorized window treatments.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

The values provided herein for the values and part numbers of the components of FIGS. 4, 5, 6, 8, 9, 10, and 11 are provided as examples only and should not limit the scope of the present invention. For example, it would be well within the capabilities of one having ordinary skill in the art to modify the values of the components of FIGS. 4, 5, 6, 8, 9, 10, and 11 and still obtain the ultrasonic receiving circuit of the present invention.

What is claimed is:

1. An ultrasonic occupancy sensor for detecting presence or absence of an occupant in a space, the occupancy sensor comprising:
   an ultrasonic transmitting circuit comprising an ultrasonic transmitting element for transmitting ultrasonic waves;
   an ultrasonic receiving circuit comprising an ultrasonic receiving element for receiving ultrasonic waves and generating an ultrasonic input signal, a synchronous rectifier for generating a rectified signal from the input signal, and a filter circuit for filtering the rectified signal to generate a filtered signal, the synchronous rectifier comprising at least one amplifier circuit and at least one analog switch coupled to an output of the amplifier circuit for forming the rectified signal; and
   a controller operable to drive the ultrasonic transmitting circuit with a drive signal to control an ultrasonic transmission frequency of the transmitted ultrasonic waves, the controller operable to render the analog switch conductive and non-conductive in phase with the drive signal to form the rectified signal, the controller further operable to receive the filtered signal and to determine that the space is occupied in response to the filtered signal.

2. The sensor of claim 1, wherein the synchronous rectifier receives a first signal representative of the input signal.

3. The sensor of claim 2, wherein the synchronous rectifier comprises a first non-inverting amplifier and a first inverting amplifier both receiving the first signal, the synchronous rectifier further comprising a first analog switch coupled to an output of the first non-inverting amplifier and a second analog switch coupled to an output of the first inverting amplifier.

4. The sensor of claim 3, wherein the synchronous rectifier further comprises a second non-inverting amplifier and a second inverting amplifier both receiving the first signal, the synchronous rectifier further comprising a third analog switch coupled to an output of the second non-inverting amplifier and a fourth analog switch coupled to an output of the second inverting amplifier, the first and second analog switches controlled to be conductive and non-conductive on a complementary basis in phase with the drive signal, the third and fourth analog switches controlled to be conductive and non-conductive on a complementary basis 90 degrees out of phase with the drive signal.

5. The sensor of claim 4, wherein outputs of the first and second analog switches are summed together to form a first rectified signal, and outputs of the third and fourth analog switches are summed together to form a second rectified signal, the filter circuit comprising a first low-pass filter for filtering the first rectified signal to generate a first filtered signal, the filter circuit further comprising a second low-pass filter for filtering the second rectified signal to generate a second filtered signal, the controller operable to receive both of the first and second filtered signals and to determine that the space is occupied in response to the first and second filtered signals.

6. The sensor of claim 3, wherein the first and second analog switches are electrically coupled together and controlled to be conductive and non-conductive in phase with the drive signal and on a complementary basis, such that outputs of the analog switches are mixed together to form the rectified signal.

7. The sensor of claim 2, wherein the synchronous rectifier comprises a first and second amplifiers, the synchronous rectifier further comprising a first analog switch coupled to an output of the first amplifier and a second analog switch coupled to an output of the second amplifier, the first analog switch controlled to be conductive and non-conductive in phase with the drive signal to form a first rectified signal, the second analog switch is controlled to be conductive and non-conductive 90 degrees out of phase with the drive signal to form a second rectified signal, the filter circuit comprising a first low-pass filter for filtering the first rectified signal to generate a first filtered signal, the filter circuit further comprising a second low-pass filter for filtering the second rectified signal to generate a second filtered signal, the controller operable to receive both of the first and second filtered signals and to determine that the space is occupied in response to the first and second filtered signals.

8. The sensor of claim 2, further comprising:
   a low phase-noise oscillator circuit coupled to the controller for setting an internal operating frequency of the controller that is approximately equal to the ultrasonic transmission frequency of the transmitted ultrasonic waves.

9. The sensor of claim 1, wherein the controller is operable to determine that the space is occupied if a magnitude of the filtered signal exceeds a threshold.

10. The sensor of claim 9, wherein the filtered signal exceeds the threshold when a received ultrasonic frequency of the received ultrasonic waves is different than the ultrasonic transmission frequency of the transmitted ultrasonic waves.

11. The sensor of claim 9, wherein the controller is operable to determine that the space is occupied if a magnitude of the filtered signal rises above an upper threshold or falls below a lower threshold.

12. The sensor of claim 1, wherein the filter circuit comprises an anti-aliasing filter, and the controller is operable to digitally filter the filtered signal from the filter prior to determining if the space is occupied.

13. An ultrasonic receiving circuit for detecting a presence or absence of an occupant in a space comprises:
   an ultrasonic receiving element for generating an ultrasonic input signal;
   a synchronous rectifier for generating a rectified signal from the input signal, the synchronous rectifier comprising at least one amplifier circuit and at least one analog switch coupled to an output of the amplifier circuit for forming the rectified signal; and
   a filter circuit for filtering the rectified signal to generate a filtered signal;
   wherein the analog switch is rendered conductive and non-conductive to form the rectified signal such that the filtered signal indicates the presence of the occupant in the space.

14. The circuit of claim 13, wherein the synchronous rectifier receives a first signal representative of the input signal, the synchronous rectifier further receiving a drive signal, the analog switch rendered conductive and non-conductive in phase with the drive signal to form the rectified signal.

15. The circuit of claim 14, wherein the synchronous rectifier comprises a first non-inverting amplifier and a first inverting amplifier both receiving the first signal, the synchronous rectifier further comprising a first analog switch coupled to an output of the first non-inverting amplifier and a second analog switch coupled to an output of the first inverting amplifier.

16. The circuit of claim 15, wherein the synchronous rectifier further comprises a second non-inverting amplifier and a second inverting amplifier both receiving the first signal, the synchronous rectifier further comprising a third analog switch coupled to an output of the second non-inverting amplifier and a fourth analog switch coupled to an output of the second inverting amplifier, the first and second analog switches controlled to be conductive and non-conductive on a complementary basis in phase with the drive signal, the third and fourth analog switches controlled to be conductive and non-conductive on a complementary basis 90 degrees out of phase with the drive signal.

17. The circuit of claim 16, wherein outputs of the first and second analog switches are summed together to form a first rectified signal, and outputs of the third and fourth analog switches are summed together to form a second rectified signal, the filter circuit comprising a first low-pass filter for filtering the first rectified signal to generate a first filtered signal, the filter circuit further comprising a second low-pass filter for filtering the second rectified signal to generate a second filtered signal, the first and second filtered signals indicating the presence of the occupant in the space.

18. The circuit of claim 15, wherein the first and second analog switches are electrically coupled together and controlled to be conductive and non-conductive in phase with the drive signal and on a complementary basis, such that outputs of the analog switches are mixed together to form the rectified signal.

19. The circuit of claim 15, wherein the synchronous rectifier receives two drive signals, the drive signals comprising square wave voltage coupled to the first and second analog switches for rendering the analog switches conductive and non-conductive on a complementary basis.

20. The circuit of claim 14, wherein the synchronous rectifier comprises a first and second amplifiers, the synchronous rectifier further comprising a first analog switch coupled to an output of the first amplifier and a second analog switch coupled to an output of the second amplifier, the first analog switch controlled to be conductive and non-conductive in phase with the drive signal to form a first rectified signal, the second analog switch is controlled to be conductive and non-conductive 90 degrees out of phase with the drive signal to form a second rectified signal, the filter circuit comprising a first low-pass filter for filtering the first rectified signal to generate a first filtered signal, the filter circuit further comprising a second low-pass filter for filtering the second rectified signal to generate a second filtered signal, the first and second filtered signals indicating the presence of the occupant in the space.

21. The circuit of claim 20, wherein the first and second amplifiers both comprise non-inverting amplifiers or both comprise inverting amplifiers.

22. The circuit of claim 14, wherein the at least one amplifier circuit of the synchronous rectifier comprises a non-inverting amplifier, the analog switch of the synchronous rectifier rendered conductive in response to the drive signal from the controller.

23. The circuit of claim 14, wherein the at least one amplifier circuit of the synchronous rectifier comprises an inverting amplifier, the analog switch of the synchronous rectifier rendered conductive in response to the inverse of the drive signal from the controller.

24. The circuit of claim 14, wherein the drive signal is characterized by low phase noise.

25. The circuit of claim 13, wherein the filtered signal indicates the presence of the occupant in the space if a magnitude of the filtered signal exceeds a threshold.

26. The circuit of claim 25, wherein the ultrasonic receiving element receives ultrasonic waves representative of whether the space is occupied or unoccupied, the filtered signal exceeding the threshold when the frequency of the received ultrasonic waves is different than the frequency of the drive signal.

27. The circuit of claim 13, wherein the filtered signal indicates the presence of the occupant in the space if the magnitude of the filtered signal rises above an upper threshold or falls below a lower threshold.

28. The circuit of claim 13, further comprising:
a second amplifier circuit for amplifying the input signal to generate an amplified signal, the synchronous rectifier receiving the amplified signal and generating the rectified signal, the second amplifier circuit comprising a non-linear amplifier operable to amplify the input signal when the magnitude of the input signal is small, and not to amplify the input signal when the magnitude of the input signal is large.

* * * * *